United States Patent
Cao

(12)
(10) Patent No.: US 6,280,955 B1
(45) Date of Patent: Aug. 28, 2001

(54) INTERLEUKIN-1 RECEPTOR ACCESSORY PROTEINS, NUCLEIC ACIDS AND METHODS

(75) Inventor: Zhaodan Cao, South San Francisco, CA (US)

(73) Assignee: Tularik Inc., South San Francisco, CA (US)

(*) Notice: Subject to any disclaimer, the term of this patent is extended or adjusted under 35 U.S.C. 154(b) by 0 days.

(21) Appl. No.: 08/991,944

(22) Filed: Dec. 16, 1997

(51) Int. Cl.[7] .................. C07K 14/705; C12N 15/12; G01N 33/53
(52) U.S. Cl. .................. 435/7.1; 435/69.1; 435/252.3; 435/320.1; 530/350; 536/23.5
(58) Field of Search .................. 435/6, 7.1, 7.2, 435/68.1, 252.3, 320.1; 530/350; 536/23.5

(56) References Cited

FOREIGN PATENT DOCUMENTS

WO 96/23067 * 1/1996 (WO) .................. C12N/15/12

* cited by examiner

Primary Examiner—John Ulm
(74) Attorney, Agent, or Firm—Richard Aron Osman

(57) ABSTRACT

The invention provides methods and compositions relating to IL-1RAcP proteins that regulate cellular signal transduction and transcriptional activation, and related nucleic acids. The polypeptides may be produced recombinantly from transformed host cells from the disclosed IL-1RAcP encoding nucleic acids purified from human cells. The invention provides isolated IL-1RAcP hybridization probes and primers capable of specifically hybridizing with the disclosed IL-1RAcP genes, IL-1RAcP-specific binding agents such as specific antibodies, and methods of making and using the subject compositions in diagnosis, therapy and in the biopharmaceutical industry.

15 Claims, 6 Drawing Sheets

| | | |
|---|---|---|
| SEQ ID NO:2 | MFLWCVVSL MFYGILQSHA SERCDDWGLD TMRQIQVFED EPARIKCPLF | 50 |
| SEQ ID NO:4 | MGLLWYLMSL SFYGILQSHA SERCDDWGLD TMRQIQVFEH EPARIKCPLF | 50 |
| hIL-1R Acp | EHFLKFNYST AHSAGLTLIW YWTRQDRDLE EPINFRLPEN RISKEKDVLW | 100 |
| mIL-1R Acp | EHFLKMNYST AHSSGLTLIW YWTRQDRDLE EPINFRLPEN RISKEKDVLW | 100 |
| hIL-1R Acp | FRPTLLNDTG NYTCMLRNTT YCSKVAFPLE VVQKDSCFNS HMKLPVHKLY | 150 |
| mIL-1R Acp | FRPTLLNDTG NYTCMLRNTT YCSKVAFPLE VVQKDSCFNS AMRFPVHKMY | 150 |
| hIL-1R Acp | IEMGIQRITC PNVDGYFPSS VKPTITWYMG CYKIQNFNNV LPEGMNLSFL | 200 |
| mIL-1R Acp | IEHGIHKITC PNVDGYFPSS VKPSVIWYKG CTEIVLFHNV LPEGMNLSFF | 200 |
| hIL-1R Acp | IALISNNGNY TCVVTYPENG RIFHLTRTLT VKVVGSPKNA MPPMIHSPND | 250 |
| mIL-1R Acp | IHLMSNNGNY TCVVTYPENG RIFHLTRHVT VKVVGSPKDA LPPQIMSPND | 250 |
| hIL-1R Acp | HVVYEKEPGE ELLIPCIVYF SFLMDSHNEV WWTIDGKKPD DITIDVTINE | 300 |
| mIL-1R Acp | RVVYEKEPGE ELMIPCKVYF SFIMDSHNEV WWTIDGKKPD DMIMDITINE | 300 |
| hIL-1R Acp | SISHSHTEDE TRTQILSIKK VTSEDLKRSY VCHARSAKGE VAKAAKVKQK | 350 |
| mIL-1R Acp | SMSMSSTEDE TRTQILSIKK VTFEDLRRNY VCHARNIKGE AEQAAKVKQK | 350 |
| hIL-1R Acp | VPAPRYTVEL ACGFGATVLL VVILIVVYHV YWLEMVLFYR AHFGTDETIL | 400 |
| mIL-1R Acp | VIHPRYTVEL ACGFGATVFL VVMLIVVYHV YWLEMVLFYR AHFGTDETIL | 400 |
| hIL-1R Acp | DGKEYDIYVS YARNAEEEEF VLLTLRGVLE NEFGYKLCIF DRDSLPGGIV | 450 |
| mIL-1R Acp | DGKEYDIYVS YARNMEEEEF VLLTLRGVLE NEFGYKLCIF DRDSLPGGIV | 450 |
| hIL-1R Acp | TDETLSFIQK SRRLLVVLSP NYVLQGTQAL LELKAGLENM ASRGNINVIL | 500 |
| mIL-1R Acp | TDETLSFIQK SRRLLVVLSP NYVLQGTQAL LELKAGLENM ASRGNINVIL | 500 |
| hIL-1R Acp | VQYKAVKETK VKELKRAKTV LTVIKWKGEK SKYPQGRFWK QLQVAMPVKK | 550 |
| mIL-1R Acp | VQYKAVKDMK VKELKRAKTV LTVIKWKGEK SKYPQGRFWK QLQVAMPVKK | 550 |
| hIL-1R Acp | SPRHSSSDEQ GLSYSSLKNV | 570 |
| mIL-1R Acp | SPRWSSNDKQ GLSYSSLKNV | 570 |

FIG. 1

| | | |
|---|---|---|
| SEQ ID NO:3 | CATTGTGCTC TAAAGCTGCC AGCATCTGGC TTTCCTAGGT TCGGCTTGGA | 50 |
| SEQ ID NO:1 | ---------- ---------- ---------- ---------- ---------- | |
| | | |
| mIL-1 AcP | CCATTGTGCT GAAAGAGGCA GTGGTCGGCC ACCCTGCATC CATCTGGTCG | 100 |
| hu IL-1R Acp | ---------- ---------- ---------- ---------- ---------- | |
| | | |
| mIL-1 AcP | CTGTCGCCGA GCCTGCTGGG CTGGCCCGAT AAGGATGGGA CTTCTGTGGT | 150 |
| hu IL-1R Acp | ---------- ---------- -----TCTCA AAGGATGACA CTTCTGTGGT | 25 |
| | | |
| mIL-1 AcP | ATTGATGAG TCTGTCTTC TATGGAATCC TGCAGAGTTA TGCTTCGGAG | 200 |
| hu IL-1R Acp | GTGTAGTGAG TCTTTACTTT TATGGAATCC TGCAAAGTTA TGCCTCAGAA | 75 |
| | | |
| mIL-1 AcP | CGCTGTGATG ACTGGGGACT AGAIACCATG GGACAAATCC AAGTGTTTGA | 250 |
| hu IL-1R Acp | CGCTGCGATG ACTGGGGACT AGACACCATG AGGCAAATCC AAGTGTTTGA | 125 |
| | | |
| mIL-1 AcP | AGATGAGCCG GCTCGAATCA AGTGCCCGCT CTTTGAACAC TTCCTGAAGT | 300 |
| hu IL-1R Acp | AGATGAGCCA GCTCGGATCA AGTGCCCACT CTTTGAACAC TTCITGAAAT | 175 |
| | | |
| mIL-1 AcP | ACAACTACAG CACTGCCCAT TCCTCTGGCC TTACCTGAT CTGGTATGG | 350 |
| hu IL-1R Acp | TCAACTACAG CACAGCCCAT TCAGCTGGCC TTACCTGAT CTGGTATTGG | 225 |
| | | |
| mIL-1 AcP | ACCAGGCAAG ACCGGGACCT GGAGGAGCCC ATTAACTTCC GCCTCCCAGA | 400 |
| hu IL-1R Acp | ACTAGGCAGG ACCGGGACCT IGAGGAGCCA ATTAACTTCC GCCTCCCGGA | 275 |
| | | |
| mIL-1 AcP | GAATCGCATC AGTAAGGAGA AAGATGTGCT GTGGTTCCGG CCCACCCTCC | 450 |
| hu IL-1R Acp | GAACCGCATT AGTAAGGAGA AAGATGTGCT GTGGTTCCGG CCCACTCTCC | 325 |
| | | |
| mIL-1 AcP | TCAATGACAC GGCAATTAC ACCTGCATGT TGAGGAACAC AACTTATGC | 500 |
| hu IL-1R Acp | TCAATGACAC TGGCAATTAT ACCTGCATGT TAAGGAACAC TACATATGC | 375 |
| | | |
| mIL-1 AcP | AGCAAAGTTG CATTTCCCT GGAAGTTGTT CAGAAGGACA GCTGTTTCAA | 550 |
| hu IL-1R Acp | AGCAAAGTTG CATTTCCCT GGAAGTTGTT CAAAAGACA GCTGTTTCAA | 425 |
| | | |
| mIL-1 AcP | TTCTGCCATG AGATTCCCAG TGCAAAGAT GTATATTGAA CATGGCATTC | 600 |
| hu IL-1R Acp | TTCCCCCATG AAACTCCCAG TGCATAAACT GTATATAGAA TATGGCATTC | 475 |
| | | |
| mIL-1 AcP | ATAAGATCAC ATGTCCAAAT GTAGAGGGAT ACTTTCCTTC CAGTGTCAAA | 650 |
| hu IL-1R Acp | AGAGGATCAC TTGTCCAAAT GTAGATGGAT ATTTTCCTTC CAGTGTCAAA | 525 |

FIG. 2A

```
mIL-1 AcP      TGTAGTACCC GAGGGTATGA ACTTGAGCTT TTTCATCCCC TTGCTTTCAA    750
hu IL-1R Acp   TGTAATACCC GAAGGTATGA ACTTGAGTTT CCTCATTGCC TTAATTTCAA    625 mIL-1 AcP      ATAAGGAAA TTACACATGT GTCGTTACAT ATCCTGAAAA CGGACGTCTC       800
hu IL-1R Acp   ATAATGGAAA TTACACATGT GTTGTTACAT ATCCAGAAAA TGGACGTACG      675 mIL-1 AcP      TTTCACTCA CCAGGACTGT GACTGTAAAG GTGGTGGCT CACCAAAGGA        850
hu IL-1R Acp   TTTCATCTCA CCAGGACTTT GACTGTAAAG GTAGTAGGCT CTCCAAAAAA      725 mIL-1 AcP      TGCATTGCCA CCCCAGATCT ATTCTCCAAA TGACCTGTTT GTCTATGAGA       900
hu IL-1R Acp   TGCAGTGCCC CCTGTGATCC ATTCACCTAA TGATCATGTG GTCTATGAGA       775 mIL-1 AcP      AAGAACCAGG AGAGGAACTG GTTATTCCCT GCAAAGTCTA TTTTAGTTTC       950
hu IL-1R Acp   AAGAACCAGG AGAGGAGCTA CTCATTCCCT GTACGGTCTA TTTTAGTTTT       825 mIL-1 AcP      ATTATGGACT CCACAATGA GGTCTGGTGG ACCATTGATG GAAATAACCC         1000
hu IL-1R Acp   CTGATGGATT CTCCAATGA GGTTTGGTGG ACCATTGATG GAAAAAAACC        875 mIL-1 AcP      TGATGACCTC ACAGTTGACA TCACTATTAA TGAAAGTCTA AGTTATTCTT       1050
hu IL-1R Acp   TGATGACATC ACTATTGATG TCACTATTAA CGAAAGTATA AGTTATAGTA       925 mIL-1 AcP      CAACGGAAGA TGAAACAAGG ACTCAGATTT TGAGCATCAA GAAAGTCACC       1100
hu IL-1R Acp   CAACAGAAGA TGAAACAAGA ACTCAGATTT TGAGCATCAA GAAAGTTACC       975 mIL-1 AcP      CCGAGGATC TCAGGCGCAA CTATGTCTGT CATGCTCGAA ATACCAAAGG        1150
hu IL-1R Acp   TCTGAGGATC TCAAGCGCAG CTATGTCTGT CATGCTAGAA GTGCCAAAGG       1025 mIL-1 AcP      GGAAGCTGAG CAGGCTGCCA AGGTGAAACA GAAAGTCATA CCACCAAGGT       1200
hu IL-1R Acp   CGAAGTTGCC AAAGCTGCCA AGGTGAAGCA GAAAGTGCCA GCTCCAAGAT       1075 mIL-1 AcP      ACACAGTAGA ACTGGCTTGT GGTTTTGGAG CCACGGTCTT TCTGGTAGTG       1250
hu IL-1R Acp   ACACAGTCGA ACTGGCTTGT GGTTTTGGAG CCACAGTCTT TCTAGTGGTG       1125 mIL-1 AcP      GTTCTCATTG TGGTTTACCA TGTTTACTGG CTGGAGATGG TCCTCTTTTA       1300
hu IL-1R Acp   ATTCTCATTG TTGTTTACCA TGTTTACTGG CTAGAGATGG TCCTATTTTA        1175
```

FIG. 2B

| | | |
|---|---|---|
| mIL-1 AcP | CTGAC CTGC GTGGAGTTTT GGAGAATGAG TTTGGATACA AGCTGTGCAT | 1450 |
| hu IL-1R Acp | CTGAC CTCC GTGGAGTTTT GGAGAATGAA TTTGGATACA AGCTGTGCAT | 1325 |
| mIL-1 AcP | CTT GAC AGA GACAG CTGC CTGGGGAAT TGTCACAGAT GAGAC CCTGA | 1500 |
| hu IL-1R Acp | CTT GAC GA GACAG TCTGC CTGGGGAAT TGTCACAGAT GAGAC TTTGA | 1375 |
| mIL-1 AcP | GCTTCATTCA GAAAAGCAGA CGA CTCCTGG TTGT CTAAG T CCCAACTAC | 1550 |
| hu IL-1R Acp | GCTTCATTCA GAAAAGCAGA CG CTCCTGG TTGT T CTAAG C CCCAACTAC | 1425 |
| mIL-1 AcP | GTGCTCCAGG GAAC A CAAGC CCTCCTGGAG CTCAAGGCTG GCCTAGAAAA | 1600 |
| hu IL-1R Acp | GTGCTCCAGG GAAC C CAAGC CCTCCTGGAG CTCAAGGCTG GCCTAGAAAA | 1475 |
| mIL-1 AcP | TATGGCCTC C CGGGGCAACA TCAACGTCAT TTTAGT CAG TACAAAGCTG | 1650 |
| hu IL-1R Acp | TATGGCCTC T CGGGGCAACA TCAACGTCAT TTTAGT A CAG TACAAAGCTG | 1525 |
| mIL-1 AcP | TGAAGGA A T GAAGGTGAAA GAGCTGAAG C GGGCTAAGAC GGTGCTCACG | 1700 |
| hu IL-1R Acp | TGAAGGA AA C GAAGGTGAAA GAGCTGAAG A GGGCTAAGAC GGTGCTCACG | 1575 |
| mIL-1 AcP | GTCATTAAAT GGAAAGG AGA AAATCCAAG TATCC T CAGG GCAGGTTCTG | 1750 |
| hu IL-1R Acp | GTCATTAAAT GGAAAGG GA AAATCCAAG TATCC A CAGG GCAGGTTCTG | 1625 |
| mIL-1 AcP | GAAGCAG TTG CAGGTGGCCA TGCCAGTGAA GAA A AGTCCC AGG T GGTCTA | 1800 |
| hu IL-1R Acp | GAAGCAG TG CAGGTGGCCA TGCCAGTGAA GAA A AGTCCC AGG GGTCTA | 1675 |
| mIL-1 AcP | GCA A TGAC AA GCAGGG CTC TC TA TCAT C C TGAAAAA GTATGAAAG | 1850 |
| hu IL-1R Acp | GCA TGA TGA GCAGGG CTC TC TA T TCAT C T TGAAAAA GTATGAAAG | 1725 |
| mIL-1 AcP | GA GAAGTGAG GGGGT A AAA GAA CAAGGCG GTTCATGGGA GG AAGG GCCC | 1900 |
| hu IL-1R Acp | GA-------- ----- A AA T GAA------ ---------- --AAGG A --- | 1740 |
| mIL-1 AcP | CCTCTTTCCT TCTAGGCTGT GGCTTCATAG ACAGAAAAAG AGTCCTGTCT | 1950 |
| hu IL-1R Acp | ---------- ---------- ---------- ---------- ---------- | 1740 |
| mIL-1 AcP | AAGCCCCCTG GGAGGAAAAT ATTCCGGGAC TGTACGCCTG GCAGCTCTGC | 2000 |
| hu IL-1R Acp | ---------- ---------- ---------- ---------- ---------- | 1740 |

FIG. 2C

| | | |
|---|---|---|
| hu IL-1R Acp | ---------- ---------- ---------- ---------- ---------- | 1740 |
| | | |
| mIL-1 AcP | CCCACCTCTG TTCTTCCCTC TTTTCTAATC TCTTCGTAAA AATCTCACCT | 2150 |
| hu IL-1R Acp | ---------- ---------- ---------- ---------- ---------- | 1740 |
| | | |
| mIL-1 AcP | CTATGGAACT GCTTTGCCCA GTGACTCAAA ACTCTGTTTA AAGATACTTT | 2200 |
| hu IL-1R Acp | ---------- ---------- ---------- ---------- ---------- | 1740 |
| | | |
| mIL-1 AcP | ACCTGCTGAC AGGAGTATCG CCTGTTTCTC AGTAGGACAC TCCTTTAATT | 2250 |
| hu IL-1R Acp | ---------- ---------- ---------- ---------- ---------- | 1740 |
| | | |
| mIL-1 AcP | TTCTCTTCTC TTCCGTCATC CATTAAGCAT GTAATCAGGG ACTAAATCTG | 2300 |
| hu IL-1R Acp | ---------- ---------- ---------- ---------- ---------- | 1740 |
| | | |
| mIL-1 AcP | TGTGAGCTGA GGCTATTTCA CTCCTTTGCT TCTGTGTCTG TTGAATCTAC | 2350 |
| hu IL-1R Acp | ---------- ---------- ---------- ---------- ---------- | 1740 |
| | | |
| mIL-1 AcP | CACCTAAGCA AGACTAACAG TCAAACTGCA GCTGTTCCTC GTGACTGATT | 2400 |
| hu IL-1R Acp | ---------- ---------- ---------- ---------- ---------- | 1740 |
| | | |
| mIL-1 AcP | AAGCGACATA CTGCCTTCCT GCTACTAAAC CCCATTCGCT CTCATCTCAG | 2450 |
| hu IL-1R Acp | ---------- ---------- ---------- ---------- ---------- | 1740 |
| | | |
| mIL-1 AcP | GTAATGGAGA TCATATTTAT AAACTTGAAA AAGCCATGGC TTTTGTTTTA | 2500 |
| hu IL-1R Acp | ---------- ---------- ---------- ---------- ---------- | 1740 |
| | | |
| mIL-1 AcP | TCATAGTAAT TTCTCATCTG TCTACAGATA GACAGGTCGG TACTTGTTCC | 2550 |
| hu IL-1R Acp | ---------- ---------- ---------- ---------- ---------- | 1740 |
| | | |
| mIL-1 AcP | TTCCTTTCCC TACCTATTGG TTCTGTCACT CATATCTCAT AGGCAGCATC | 2600 |
| hu IL-1R Acp | ---------- ---------- ---------- ---------- ---------- | 1740 |
| | | |
| mIL-1 AcP | ACGCTTGCTG CGGTCTGCGG GGAAGCTTTA ATGGTGCTAA TGGAGAGTGA | 2650 |
| hu IL-1R Acp | ---------- ---------- ---------- ---------- ---------- | 1740 |
| | | |
| mIL-1 AcP | GAAAATCCAA AAGCGCTCTC AGGGCATTTT TCACATGGGA AGAGAGCACA | 2700 |
| hu IL-1R Acp | ---------- ---------- ---------- ---------- ---------- | 1740 |

FIG. 2D

```
mIL-1 AcP      ACCAGGAAAA GTGGTTAATC CTCACTCCTT CACACACCTC TTCATTATGA    2800
hu IL-1R Acp   ---------- ---------- ---------- ---------- ----------    1740 mIL-1 AcP      AGTGGAGGTG AGAGGTACTG AGTTTCCTTT TGGCATTACT ATTCCAAAAG    2850
hu IL-1R Acp   ---------- ---------- ---------- ---------- ----------    1740 mIL-1 AcP      GAATGATTAT TCATGGTAAT TAATTGTGCA GTGCCTGTAG TACCTTGCTC    2900
hu IL-1R Acp   ---------- ---------- ---------- ---------- ----------    1740 mIL-1 AcP      CAAATGGATC ACCCTGCAAA TCATTAATAA TGAAGTGGTT TTATTAGTTT    2950
hu IL-1R Acp   ---------- ---------- ---------- ---------- ----------    1740 mIL-1 AcP      CAAGCAGAAT TCACTATTT CTCAGACTTC CAAAAGTGAA AGGCAAGTAT    3000
hu IL-1R Acp   ---------- ---------- ---------- ---------- ----------    1740 mIL-1 AcP      AACATTCACA TTTAGAGAGG CCAATTTCTA TTTCATATCT AACATGTATA    3050
hu IL-1R Acp   ---------- ---------- ---------- ---------- ----------    1740 mIL-1 AcP      TATATGTATA TACATATATA CATATATATA TGATCTCTGT ACACATAAAT    3100
hu IL-1R Acp   ---------- ---------- ---------- ---------- ----------    1740 mIL-1 AcP      TTTATATGTC TATGTATATA GAAGTATCCA CAAATGACAT GTGTGTGTGT    3150
hu IL-1R Acp   ---------- ---------- ---------- ---------- ----------    1740 mIL-1 AcP      ATATCCACCT GCCTATAAAT TATCTCTGTG TATTATTTTG GGCTATACAT    3200
hu IL-1R Acp   ---------- ---------- ---------- ---------- ----------    1740 mIL-1 AcP      AATCACACAC ATACATCTTT CAGTAGTCAT TGGCAAAATA TTGAAAGCCA    3250
hu IL-1R Acp   ---------- ---------- ---------- ---------- ----------    1740 mIL-1 AcP      GTAGAACTAG TGTTCAATCT TTAAATTATG TTAATAGTGT TATGGTTTTG    3300
hu IL-1R Acp   ---------- ---------- ---------- ---------- ----------    1740 mIL-1 AcP      TGTTGATATT TTCATTTCAT TTCATTTCTG TTCCATTTGT GAATTCCCTT    3350
hu IL-1R Acp   ---------- ---------- ---------- ---------- ----------    1740 mIL-1 AcP      TAGAGTHABV RRTNRMAT                                        3368
hu IL-1R Acp   ---------- --------                                        1740
```

FIG. 2E

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1740 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 10..1719

(xi) SEQUENCE DESCRIPTION: SEQ ID NO:1:

```
TCTCAAAGG ATG ACA CTT CTG TGG TGT GTA GTG AGT CTC TAC TTT TAT         48
          Met Thr Leu Leu Trp Cys Val Val Ser Leu Tyr Phe Tyr
            1               5                  10

GGA ATC CTG CAA AGT GAT GCC TCA GAA CGC TGC GAT GAC TGG GGA CTA        96
Gly Ile Leu Gln Ser Asp Ala Ser Glu Arg Cys Asp Asp Trp Gly Leu
         15                  20                  25

GAC ACC ATG AGG CAA ATC CAA GTG TTT GAA GAT GAG CCA GCT CGC ATC       144
Asp Thr Met Arg Gln Ile Gln Val Phe Glu Asp Glu Pro Ala Arg Ile
 30                  35                  40                  45

AAG TGC CCA CTC TTT GAA CAC TTC TTG AAA TTC AAC TAC AGC ACA GCC       192
Lys Cys Pro Leu Phe Glu His Phe Leu Lys Phe Asn Tyr Ser Thr Ala
                     50                  55                  60

CAT TCA GCT GGC CTT ACT CTG ATC TGG TAT TGG ACT AGG CAG GAC CGG       240
His Ser Ala Gly Leu Thr Leu Ile Trp Tyr Trp Thr Arg Gln Asp Arg
             65                  70                  75

GAC CTT GAG GAG CCA ATT AAC TTC CGC CTC CCC GAG AAC CGC ATT AGT       288
Asp Leu Glu Glu Pro Ile Asn Phe Arg Leu Pro Glu Asn Arg Ile Ser
 80                  85                  90
```

-continued

| | |
|---|---|
| AAG GAG AAA GAT GTG CTG TGG TTC CGG CCC ACT CTC CTC AAT GAC ACT<br>Lys Glu Lys Asp Val Leu Trp Phe Arg Pro Thr Leu Leu Asn Asp Thr<br>        95                        100                       105 | 336 |
| GGC AAC TAT ACC TGC ATG TTA AGG AAC ACT ACA TAT TGC AGC AAA GTT<br>Gly Asn Tyr Thr Cys Met Leu Arg Asn Thr Thr Tyr Cys Ser Lys Val<br>110                       115                     120                     125 | 384 |
| GCA TTT CCC TTG GAA GTT GTT CAA AAA GAC AGC TGT TTC AAT TCC CCC<br>Ala Phe Pro Leu Glu Val Val Gln Lys Asp Ser Cys Phe Asn Ser Pro<br>                        130                     135                     140 | 432 |
| ATG AAA CTC CCA GTG CAT AAA CTG TAT ATA GAA TAT GGC ATT CAG AGG<br>Met Lys Leu Pro Val His Lys Leu Tyr Ile Glu Tyr Gly Ile Gln Arg<br>             145                     150                     155 | 480 |
| ATC ACT TGT CCA AAT GTA GAT GGA TAT TTT CCT TCC AGT GTC AAA CCG<br>Ile Thr Cys Pro Asn Val Asp Gly Tyr Phe Pro Ser Ser Val Lys Pro<br>                160                     165                     170 | 528 |
| ACT ATC ACT TGG TAT ATG GGC TGT TAT AAA ATA CAG AAT TTT AAT AAT<br>Thr Ile Thr Trp Tyr Met Gly Cys Tyr Lys Ile Gln Asn Phe Asn Asn<br>         175                       180                     185 | 576 |
| GTA ATA CCC GAA GGT ATG AAC TTG AGT TTC CTC ATT GCC TTA ATT TCA<br>Val Ile Pro Glu Gly Met Asn Leu Ser Phe Leu Ile Ala Leu Ile Ser<br>190                       195                     200                     205 | 624 |
| AAT AAT GGA AAT TAC ACA TGT GTT GTT ACA TAT CCA GAA AAT GGA CGT<br>Asn Asn Gly Asn Tyr Thr Cys Val Val Thr Tyr Pro Glu Asn Gly Arg<br>                        210                     215                     220 | 672 |
| ACG TTT CAT CTC ACC AGG ACT CTG ACT GTA AAG GTA GTA GGC TCT CCA<br>Thr Phe His Leu Thr Arg Thr Leu Thr Val Lys Val Val Gly Ser Pro<br>             225                     230                     235 | 720 |
| AAA AAT GCA GTG CCC CCT GTG ATC CAT TCA CCT AAT GAT CAT GTG GTC<br>Lys Asn Ala Val Pro Pro Val Ile His Ser Pro Asn Asp His Val Val<br>                240                     245                     250 | 768 |
| TAT GAG AAA GAA CCA GGA GAG GAG CTA CTC ATT CCC TGT ACG GTC TAT<br>Tyr Glu Lys Glu Pro Gly Glu Glu Leu Leu Ile Pro Cys Thr Val Tyr<br>         255                       260                     265 | 816 |
| TTT AGT TTT CTG ATG GAT TCT CGC AAT GAG GTT TGG TGG ACC ATT GAT<br>Phe Ser Phe Leu Met Asp Ser Arg Asn Glu Val Trp Trp Thr Ile Asp<br>270                       275                     280                     285 | 864 |
| GGA AAA AAA CCT GAT GAC ATC ACT ATT GAT GTC ACC ATT AAC GAA AGT<br>Gly Lys Lys Pro Asp Asp Ile Thr Ile Asp Val Thr Ile Asn Glu Ser<br>                        290                     295                     300 | 912 |
| ATA AGT CAT AGT AGA ACA GAA GAT GAA ACA AGA ACT CAG ATT TTG AGC<br>Ile Ser His Ser Arg Thr Glu Asp Glu Thr Arg Thr Gln Ile Leu Ser<br>             305                     310                     315 | 960 |
| ATC AAG AAA GTT ACC TCT GAG GAT CTC AAG CGC AGC TAT GTC TGT CAT<br>Ile Lys Lys Val Thr Ser Glu Asp Leu Lys Arg Ser Tyr Val Cys His<br>         320                       325                     330 | 1008 |
| GCT AGA AGT GCC AAA GGC GAA GTT GCC AAA GCA GCC AAG GTG AAG CAG<br>Ala Arg Ser Ala Lys Gly Glu Val Ala Lys Ala Ala Lys Val Lys Gln<br>335                       340                     345 | 1056 |
| AAA GTG CCA GCT CCA AGA TAC ACA GTG GAA CTG GCT TGT GGT TTT GGA<br>Lys Val Pro Ala Pro Arg Tyr Thr Val Glu Leu Ala Cys Gly Phe Gly<br>350                       355                     360                     365 | 1104 |
| GCC ACA GTC CTG CTA GTG GTG ATT CTC ATT GTT GTT TAC CAT GTT TAC<br>Ala Thr Val Leu Leu Val Val Ile Leu Ile Val Val Tyr His Val Tyr<br>                        370                     375                     380 | 1152 |
| TGG CTA GAG ATG GTC CTA TTT TAC CGG GCT CAT TTT GGA ACA GAT GAA<br>Trp Leu Glu Met Val Leu Phe Tyr Arg Ala His Phe Gly Thr Asp Glu<br>             385                     390                     395 | 1200 |
| ACC ATT TTA GAT GGA AAA GAG TAT GAT ATT TAT GTA TCC TAT GCA AGG<br>Thr Ile Leu Asp Gly Lys Glu Tyr Asp Ile Tyr Val Ser Tyr Ala Arg | 1248 |

-continued

```
                400                 405                 410
AAT GCG GAA GAA GAA GAA TTT GTA TTA CTG ACC CTC CGT GGA GTT TTG        1296
Asn Ala Glu Glu Glu Glu Phe Val Leu Leu Thr Leu Arg Gly Val Leu
        415                 420                 425

GAG AAT GAA TTT GGA TAC AAG CTG TGC ATC TTT GAC CGA GAC AGT CTG        1344
Glu Asn Glu Phe Gly Tyr Lys Leu Cys Ile Phe Asp Arg Asp Ser Leu
430                 435                 440                 445

CCT GGG GGA ATT GTC ACA GAT GAG ACT TTG AGC TTC ATT CAG AAA AGC        1392
Pro Gly Gly Ile Val Thr Asp Glu Thr Leu Ser Phe Ile Gln Lys Ser
                450                 455                 460

AGA CGC CTC CTG GTT GTT CTA AGC CCC AAC TAC GTG CTC CAG GGA ACC        1440
Arg Arg Leu Leu Val Val Leu Ser Pro Asn Tyr Val Leu Gln Gly Thr
            465                 470                 475

CAA GCC CTC CTG GAG CTC AAG GCT GGC CTA GAA AAT ATG GCC TCT CGG        1488
Gln Ala Leu Leu Glu Leu Lys Ala Gly Leu Glu Asn Met Ala Ser Arg
        480                 485                 490

GGC AAC ATC AAC GTC ATT TTA GTA CAG TAC AAA GCT GTG AAG GAA ACG        1536
Gly Asn Ile Asn Val Ile Leu Val Gln Tyr Lys Ala Val Lys Glu Thr
    495                 500                 505

AAG GTG AAA GAG CTG AAG AGG GCT AAG ACG GTC CTC ACG GTC ATT AAA        1584
Lys Val Lys Glu Leu Lys Arg Ala Lys Thr Val Leu Thr Val Ile Lys
510                 515                 520                 525

TGG AAA GGG GAA AAA TCC AAG TAT CCA CAG GGC AGG TTC TGG AAG CAG        1632
Trp Lys Gly Glu Lys Ser Lys Tyr Pro Gln Gly Arg Phe Trp Lys Gln
                530                 535                 540

CTG CAG GTG GCC ATG CCA GTG AAG AAA AGT CCC AGG CGG TCT AGC AGT        1680
Leu Gln Val Ala Met Pro Val Lys Lys Ser Pro Arg Arg Ser Ser Ser
            545                 550                 555

GAT GAG CAG GGC CTC TCG TAT TCA TCT TTG AAA AAT GTA TGAAAGGAAT        1729
Asp Glu Gln Gly Leu Ser Tyr Ser Ser Leu Lys Asn Val
        560                 565                 570

AATGAAAAGG A                                                           1740
```

(2) INFORMATION FOR SEQ ID NO:2:

(i) SEQUENCE CHARACTERISTICS:
        (A) LENGTH: 570 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125
```

-continued

```
Leu Glu Val Val Gln Lys Asp Ser Cys Phe Asn Ser Pro Met Lys Leu
    130                 135                 140
Pro Val His Lys Leu Tyr Ile Glu Tyr Gly Ile Gln Arg Ile Thr Cys
145                 150                 155                 160
Pro Asn Val Asp Gly Tyr Phe Pro Ser Ser Val Lys Pro Thr Ile Thr
                165                 170                 175
Trp Tyr Met Gly Cys Tyr Lys Ile Gln Asn Phe Asn Asn Val Ile Pro
                180                 185                 190
Glu Gly Met Asn Leu Ser Phe Leu Ile Ala Leu Ile Ser Asn Asn Gly
                195                 200                 205
Asn Tyr Thr Cys Val Val Thr Tyr Pro Glu Asn Gly Arg Thr Phe His
    210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
                260                 265                 270
Leu Met Asp Ser Arg Asn Glu Val Trp Trp Thr Ile Asp Gly Lys Lys
                275                 280                 285
Pro Asp Asp Ile Thr Ile Asp Val Thr Ile Asn Glu Ser Ile Ser His
                290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
                340                 345                 350
Ala Pro Arg Tyr Thr Val Glu Leu Ala Cys Gly Phe Gly Ala Thr Val
                355                 360                 365
Leu Leu Val Val Ile Leu Ile Val Val Tyr His Val Tyr Trp Leu Glu
                370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Ala Glu
                405                 410                 415
Glu Glu Glu Phe Val Leu Leu Thr Leu Arg Gly Val Leu Glu Asn Glu
                420                 425                 430
Phe Gly Tyr Lys Leu Cys Ile Phe Asp Arg Asp Ser Leu Pro Gly Gly
                435                 440                 445
Ile Val Thr Asp Glu Thr Leu Ser Phe Ile Gln Lys Ser Arg Arg Leu
    450                 455                 460
Leu Val Val Leu Ser Pro Asn Tyr Val Leu Gln Gly Thr Gln Ala Leu
465                 470                 475                 480
Leu Glu Leu Lys Ala Gly Leu Glu Asn Met Ala Ser Arg Gly Asn Ile
                485                 490                 495
Asn Val Ile Leu Val Gln Tyr Lys Ala Val Lys Glu Thr Lys Val Lys
                500                 505                 510
Glu Leu Lys Arg Ala Lys Thr Val Leu Thr Val Ile Lys Trp Lys Gly
                515                 520                 525
Glu Lys Ser Lys Tyr Pro Gln Gly Arg Phe Trp Lys Gln Leu Gln Val
                530                 535                 540
```

```
Ala Met Pro Val Lys Lys Ser Pro Arg Arg Ser Ser Asp Glu Gln
545                 550                 555                 560

Gly Leu Ser Tyr Ser Ser Leu Lys Asn Val
                565                 570

(2) INFORMATION FOR SEQ ID NO:3:

(i) SEQUENCE CHARACTERISTICS:
        (A) LENGTH: 3355 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 135..1844

(xi) SEQUENCE DESCRIPTION: SEQ ID NO:3:

CATTGTGCTC TAAAGCTGCC AGCATCTGGC TTTCCTAGGT TCGGCTTGGA CCATTGTGCT        60

GAAAGAGGCA GTGGTCGGCC ACCCTGCATC CATCTGGTCG CTGTCGCCGA GCCTGCTGGG       120

CTGGCCCGAT AAGG ATG GGA CTT CTG TGG TAT TTG ATG AGT CTG TCC TTC         170
              Met Gly Leu Leu Trp Tyr Leu Met Ser Leu Ser Phe
                                575                 580

TAT GGG ATC CTG CAG AGT CAT GCT TCG GAG CGC TGT GAT GAC TGG GGA         218
Tyr Gly Ile Leu Gln Ser His Ala Ser Glu Arg Cys Asp Asp Trp Gly
            585                 590                 595

CTA GAT ACC ATG CGA CAA ATC CAA GTG TTT GAA GAT GAG CCG GCT CGA         266
Leu Asp Thr Met Arg Gln Ile Gln Val Phe Glu Asp Glu Pro Ala Arg
        600                 605                 610

ATC AAG TGC CCC CTC TTT GAA CAC TTC CTG AAG TAC AAC TAC AGC ACT         314
Ile Lys Cys Pro Leu Phe Glu His Phe Leu Lys Tyr Asn Tyr Ser Thr
615                 620                 625                 630

GCC CAT TCC TCT GGC CTT ACC CTG ATC TGG TAC TGG ACC AGG CAA GAC         362
Ala His Ser Ser Gly Leu Thr Leu Ile Trp Tyr Trp Thr Arg Gln Asp
                635                 640                 645

CGG GAC CTG GAG GAG CCC ATT AAC TTC CGC CTC CCA GAG AAT CGC ATC         410
Arg Asp Leu Glu Glu Pro Ile Asn Phe Arg Leu Pro Glu Asn Arg Ile
            650                 655                 660

AGT AAG GAG AAA GAT GTG CTC TGG TTC CGG CCC ACC CTC CTC AAT GAC         458
Ser Lys Glu Lys Asp Val Leu Trp Phe Arg Pro Thr Leu Leu Asn Asp
        665                 670                 675

ACG GGC AAT TAC ACC TGC ATG TTG AGG AAC ACA ACT TAC TGC AGC AAA         506
Thr Gly Asn Tyr Thr Cys Met Leu Arg Asn Thr Thr Tyr Cys Ser Lys
    680                 685                 690

GTT GCA TTT CCC CTG GAA GTT GTT CAG AAG GAC AGC TGT TTC AAT TCT         554
Val Ala Phe Pro Leu Glu Val Val Gln Lys Asp Ser Cys Phe Asn Ser
695                 700                 705                 710

GCC ATG AGA TTC CCA GTG CAC AAG ATG TAT ATT GAA CAT GGC ATT CAT         602
Ala Met Arg Phe Pro Val His Lys Met Tyr Ile Glu His Gly Ile His
                715                 720                 725

AAG ATC ACA TGT CCA AAT GTA GAC GGA TAC TTT CCT TCC AGT GTC AAA         650
Lys Ile Thr Cys Pro Asn Val Asp Gly Tyr Phe Pro Ser Ser Val Lys
            730                 735                 740

CCA TCG GTC ACT TGG TAT AAG GGT TGT ACT GAA ATA GTG GAC TTT CAT         698
Pro Ser Val Thr Trp Tyr Lys Gly Cys Thr Glu Ile Val Asp Phe His
        745                 750                 755

AAT GTA CTA CCC GAG GGC ATG AAC TTG AGC TTT TTC ATC CCC TTG GTT         746
Asn Val Leu Pro Glu Gly Met Asn Leu Ser Phe Phe Ile Pro Leu Val
    760                 765                 770
```

```
                                                    -continued
TCA AAT AAC GGA AAT TAC ACA TGT GTG GTT ACA TAT CCT GAA AAC GGA        794
Ser Asn Asn Gly Asn Tyr Thr Cys Val Val Thr Tyr Pro Glu Asn Gly
775             780                 785                 790

CGT CTC TTT CAC CTC ACC AGG ACT GTG ACT GTA AAG GTG GTG GGC TCA        842
Arg Leu Phe His Leu Thr Arg Thr Val Thr Val Lys Val Val Gly Ser
                795                 800                 805

CCA AAG GAT GCA TTG CCA CCC CAG ATC TAT TCT CCA AAT GAC CGT GTT        890
Pro Lys Asp Ala Leu Pro Pro Gln Ile Tyr Ser Pro Asn Asp Arg Val
            810                 815                 820

GTC TAT GAG AAA GAA CCA GGA GAG GAA CTG GTT ATT CCC TGC AAA GTC        938
Val Tyr Glu Lys Glu Pro Gly Glu Glu Leu Val Ile Pro Cys Lys Val
        825                 830                 835

TAT TTC AGT TTC ATT ATG GAC TCC CAC AAT GAG GTC TGG TGG ACC ATT        986
Tyr Phe Ser Phe Ile Met Asp Ser His Asn Glu Val Trp Trp Thr Ile
    840                 845                 850

GAT GGA AAG AAG CCT GAT GAC GTC ACA GTC GAC ATC ACT ATT AAT GAA       1034
Asp Gly Lys Lys Pro Asp Asp Val Thr Val Asp Ile Thr Ile Asn Glu
855                 860                 865                 870

AGT GTA AGT TAT TCT TCA ACG GAA GAT GAA ACA AGG ACT CAG ATT TTG       1082
Ser Val Ser Tyr Ser Ser Thr Glu Asp Glu Thr Arg Thr Gln Ile Leu
                875                 880                 885

AGC ATC AAG AAA GTC ACC CCG GAG GAT CTC AGG CGC AAC TAT GTC TGT       1130
Ser Ile Lys Lys Val Thr Pro Glu Asp Leu Arg Arg Asn Tyr Val Cys
            890                 895                 900

CAT GCT CGA AAT ACC AAA GGG GAA GCT GAG CAG GCT GCC AAG GTG AAA       1178
His Ala Arg Asn Thr Lys Gly Glu Ala Glu Gln Ala Ala Lys Val Lys
        905                 910                 915

CAG AAA GTC ATA CCA CCA AGG TAC ACA GTA GAA CTC GCC TGT GGT TTT       1226
Gln Lys Val Ile Pro Pro Arg Tyr Thr Val Glu Leu Ala Cys Gly Phe
    920                 925                 930

GGA GCC ACG GTC TTT CTG GTA GTG GTT CTC ATT GTG GTT TAC CAT GTT       1274
Gly Ala Thr Val Phe Leu Val Val Val Leu Ile Val Val Tyr His Val
935                 940                 945                 950

TAC TGG CTG GAG ATG GTC CTC TTT TAC CGA GCT CAC TTT GGA ACA GAT       1322
Tyr Trp Leu Glu Met Val Leu Phe Tyr Arg Ala His Phe Gly Thr Asp
                955                 960                 965

GAA ACA ATT CTT GAT GGA AAG GAG TAT GAT ATT TAT GTT TCC TAT GCA       1370
Glu Thr Ile Leu Asp Gly Lys Glu Tyr Asp Ile Tyr Val Ser Tyr Ala
            970                 975                 980

AGA AAT GTG GAA GAA GAG GAA TTT GTG CTG CTG ACG CTG CGT GGA GTT       1418
Arg Asn Val Glu Glu Glu Glu Phe Val Leu Leu Thr Leu Arg Gly Val
        985                 990                 995

TTG GAG AAT GAG TTT GGA TAC AAG CTG TGC ATC TTC GAC AGA GAC AGC       1466
Leu Glu Asn Glu Phe Gly Tyr Lys Leu Cys Ile Phe Asp Arg Asp Ser
    1000                1005                1010

CTG CCT GGG GGA ATT GTC ACA GAT GAG ACC CTG AGC TTC ATT CAG AAA       1514
Leu Pro Gly Gly Ile Val Thr Asp Glu Thr Leu Ser Phe Ile Gln Lys
1015                1020                1025                1030

AGC AGA CGA CTC CTG GTT GTC CTA AGT CCC AAC TAC GTG CTC CAG GGA       1562
Ser Arg Arg Leu Leu Val Val Leu Ser Pro Asn Tyr Val Leu Gln Gly
                1035                1040                1045

ACA CAA GCC CTC CTG GAG CTC AAG GCT GGC TTA GAA AAT ATG GCC TCC       1610
Thr Gln Ala Leu Leu Glu Leu Lys Ala Gly Leu Glu Asn Met Ala Ser
            1050                1055                1060

CGG GGC AAC ATC AAC GTC ATT TTA GTG CAG TAC AAA GCT GTG AAG GAC       1658
Arg Gly Asn Ile Asn Val Ile Leu Val Gln Tyr Lys Ala Val Lys Asp
        1065                1070                1075

ATG AAG GTG AAA GAG CTG AAG CGG GCT AAG ACG GTG CTC ACG GTC ATT       1706
Met Lys Val Lys Glu Leu Lys Arg Ala Lys Thr Val Leu Thr Val Ile
    1080                1085                1090
```

| | | |
|---|---|---|
| AAA TGG AAA GGA GAG AAA TCC AAG TAT CCT CAG GGC AGG TTC TGG AAG<br>Lys Trp Lys Gly Glu Lys Ser Lys Tyr Pro Gln Gly Arg Phe Trp Lys<br>1095                              1100                 1105                    1110 | 1754 |
| CAG TTG CAG GTG GCC ATG CCA GTG AAG AAG AGT CCC AGG TGG TCT AGC<br>Gln Leu Gln Val Ala Met Pro Val Lys Lys Ser Pro Arg Trp Ser Ser<br>                 1115                    1120                     1125 | 1802 |
| AAT GAC AAG CAG GGT CTC TCC TAC TCA TCC CTG AAA AAC GTA<br>Asn Asp Lys Gln Gly Leu Ser Tyr Ser Ser Leu Lys Asn Val<br>              1130                  1135               1140 | 1844 |
| TGAAAGGAGA AGTGAGGGGG TACAAAGAAC AAGGCGGTTC ATGGGAGGAA GGGCCCCCTC | 1904 |
| TTTCCTTCTA GGCTGTGGCT TCATAGACAG AAAAAGAGTC CTGTCTAAGC CCCCTGGGAG | 1964 |
| GAAAATATTC CGGGACTGTA CGCCTGGCAG CTCTGCCTCT CAGCAATACT AAGCGTTACA | 2024 |
| GTGATGGACT CCACAGTCCG CCACCAGTTC TAAAAGTCAT TTTGATCTTT ACAAGTAAAG | 2084 |
| ATGTGTCTGA TGCACCCCCA CCTCTGTTCT TCCCTCTTTT CTAATCTCTT CGTAAAAATC | 2144 |
| TCACCTCTAT GGAACTGCTT TGCCCAGTGA CTCAAAACTC TGTTTAAAGA TACTTTACCT | 2204 |
| GCTGACAGGA GTATCGCCTG TTTCTCAGTA GGACACTCCT TTAATTTTCT CTTCTCTTCC | 2264 |
| GTCATCCATT AAGCATGTAA TCAGGGACTA AATCTGTGTG AGCTGAGGCT ATTTCACTCC | 2324 |
| TTTGCTTCTG TGTCTGTTGA ATCTACCACC TAAGCAAGAC TAACAGTCAA ACTGCAGCTG | 2384 |
| TTCCTCGTGA CTGATTAAGC GACATACTGC CTTCCTGCTA CTAAACCCCA TTCGCTCTCA | 2444 |
| TCTCAGGTAA TGGAGATCAT ATTTATAAAC TTGAAAAAGC CATGGCTTTT GTTTTATCAT | 2504 |
| AGTAATTTCT CATCTGTCTA CAGATAGACA GGTCGGTACT TGTTCCTTCC TTTCCCTACC | 2564 |
| TATTGGTTCT GTCACTCATA TCTCATAGGC AGCATCACGC TTGCTGCGGT CTGCGGGAA | 2624 |
| GCTTTAATGG TGCTAATGGA GAGTGAGAAA ATCCAAAAGC GCTCTCAGGG CATTTTTCAC | 2684 |
| ATGGAAGAG AGCACAGAAG AGAATGCTTG GCGGTTTGTT TGTTAATTCT GACCCTAGAG | 2744 |
| GGGAAAACCA GGAAAAGTGG TTAATCCTCA CTCCTTCACA CACCTCTTCA TTATGAAGTG | 2804 |
| GAGGTGAGAG GTACTGAGTT TCCTTTTGGC ATTACTATTC CAAAAGGAAT GATTATTCAT | 2864 |
| GGTAATTAAT TGTGCAGTGC CTGTAGTACC TTGCTCCAAA TGGATCACCC TGCAAATCAT | 2924 |
| TAATAATGAA GTGGTTTTAT TAGTTTCAAG CAGAATTTCA CTATTTCTCA GACTTCCAAA | 2984 |
| AGTGAAAGGC AAGTATAACA TTCACATTTA GAGAGGCCAA TTTCTATTTC ATATCTAACA | 3044 |
| TGTATATATA TGTATATACA TATATACATA TATATATGAT CTCTGTACAC ATAAATTTTA | 3104 |
| TATGTCTATG TATATAGAAG TATCCACAAA TGACATGTGT GTGTGTATAT CCACCTGCCT | 3164 |
| ATAAATTATC TCTGTGTATT ATTTTGGGCT ATACATAATC ACACACATAC ATCTTTCAGT | 3224 |
| AGTCATTGGC AAAATATTGA AAGCCAGTAG AACTAGTGTT CAATCTTTAA ATTATGTTAA | 3284 |
| TAGTGTTATG GTTTTGTGTT GATATTTTCA TTTCATTTCA TTTCTGTTCC ATTTGTGAAT | 3344 |
| TCCCTTTAGA G | 3355 |

(2) INFORMATION FOR SEQ ID NO:4:

(i) SEQUENCE CHARACTERISTICS:
        (A) LENGTH: 570 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Leu Leu Trp Tyr Leu Met Ser Leu Ser Phe Tyr Gly Ile Leu
 1             5                 10                15

```
Gln Ser His Ala Ser Glu Arg Cys Asp Asp Trp Gly Leu Asp Thr Met
             20                  25                  30
Arg Gln Ile Gln Val Phe Glu Asp Glu Pro Ala Arg Ile Lys Cys Pro
         35                  40                  45
Leu Phe Glu His Phe Leu Lys Tyr Asn Tyr Ser Thr Ala His Ser Ser
     50                  55                  60
Gly Leu Thr Leu Ile Trp Tyr Trp Thr Arg Gln Asp Arg Asp Leu Glu
 65                  70                  75                  80
Glu Pro Ile Asn Phe Arg Leu Pro Glu Asn Arg Ile Ser Lys Glu Lys
                 85                  90                  95
Asp Val Leu Trp Phe Arg Pro Thr Leu Leu Asn Asp Thr Gly Asn Tyr
             100                 105                 110
Thr Cys Met Leu Arg Asn Thr Thr Tyr Cys Ser Lys Val Ala Phe Pro
         115                 120                 125
Leu Glu Val Val Gln Lys Asp Ser Cys Phe Asn Ser Ala Met Arg Phe
     130                 135                 140
Pro Val His Lys Met Tyr Ile Glu His Gly Ile His Lys Ile Thr Cys
145                 150                 155                 160
Pro Asn Val Asp Gly Tyr Phe Pro Ser Ser Val Lys Pro Ser Val Thr
                 165                 170                 175
Trp Tyr Lys Gly Cys Thr Glu Ile Val Asp Phe His Asn Val Leu Pro
             180                 185                 190
Glu Gly Met Asn Leu Ser Phe Phe Ile Pro Leu Val Ser Asn Asn Gly
         195                 200                 205
Asn Tyr Thr Cys Val Val Thr Tyr Pro Glu Asn Gly Arg Leu Phe His
     210                 215                 220
Leu Thr Arg Thr Val Thr Val Lys Val Val Gly Ser Pro Lys Asp Ala
225                 230                 235                 240
Leu Pro Pro Gln Ile Tyr Ser Pro Asn Asp Arg Val Val Tyr Glu Lys
                 245                 250                 255
Glu Pro Gly Glu Glu Leu Val Ile Pro Cys Lys Val Tyr Phe Ser Phe
             260                 265                 270
Ile Met Asp Ser His Asn Glu Val Trp Trp Thr Ile Asp Gly Lys Lys
         275                 280                 285
Pro Asp Asp Val Thr Val Asp Ile Thr Ile Asn Glu Ser Val Ser Tyr
     290                 295                 300
Ser Ser Thr Glu Asp Glu Thr Arg Thr Gln Ile Leu Ser Ile Lys Lys
305                 310                 315                 320
Val Thr Pro Glu Asp Leu Arg Arg Asn Tyr Val Cys His Ala Arg Asn
                 325                 330                 335
Thr Lys Gly Glu Ala Glu Gln Ala Ala Lys Val Lys Gln Lys Val Ile
             340                 345                 350
Pro Pro Arg Tyr Thr Val Glu Leu Ala Cys Gly Phe Gly Ala Thr Val
         355                 360                 365
Phe Leu Val Val Val Leu Ile Val Val Tyr His Val Tyr Trp Leu Glu
     370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Val Glu
                 405                 410                 415
Glu Glu Glu Phe Val Leu Leu Thr Leu Arg Gly Val Leu Glu Asn Glu
             420                 425                 430
```

―continued

```
Phe Gly Tyr Lys Leu Cys Ile Phe Asp Arg Asp Ser Leu Pro Gly Gly
        435                 440                 445

Ile Val Thr Asp Glu Thr Leu Ser Phe Ile Gln Lys Ser Arg Arg Leu
        450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
            485                 490                 495

Asn Val Ile Leu Val Gln Tyr Lys Ala Val Lys Asp Met Lys Val Lys
            500                 505                 510

Glu Leu Lys Arg Ala Lys Thr Val Leu Thr Val Ile Lys Trp Lys Gly
        515                 520                 525

Glu Lys Ser Lys Tyr Pro Gln Gly Arg Phe Trp Lys Gln Leu Gln Val
        530                 535                 540

Ala Met Pro Val Lys Lys Ser Pro Arg Trp Ser Ser Asn Asp Lys Gln
545                 550                 555                 560

Gly Leu Ser Tyr Ser Ser Leu Lys Asn Val
                565                 570
```

INTERLEUKIN-1 RECEPTOR ACCESSORY PROTEINS, NUCLEIC ACIDS AND METHODS

INTRODUCTION

1. Field of the Invention

The field of this invention is proteins involved in IL-1-mediated cell signal transduction.

2. Background

Interleukin-1 (IL-1) plays a central role in the generation of inflammatory responses (1). After binding to the cell surface receptor IL-1RI, IL-1 activates intracellular signaling cascades leading to the activation of the transcription factor NF-κB, which in turn upregulates the expression of many proinflammatory genes in the nucleus (1, 2). Although considerable progress has been made recently in delineating IL-1 signaling mechanism, our understanding of the process (es) remains incomplete. Within seconds after cells are exposed to IL-1, IL-1 receptor associated kinase (IRAK) is recruited in the IL-1 receptor complex where it becomes highly phosphorylated (3). Subsequently, IRAK interacts with TRAF6, a TRAF family member required for IL-1 mediated NF-κB activation (4). IRAK and IL-IRI do not interact directly with one another in mammalian cells when the two proteins are coexpressed, nor do they interact in the yeast two hybrid system (8).

We have found a protein, IL-1R accessory protein, IL-1RAcP, that is necessary for the recruitment of IRAK to the receptor complex. IL-1RAcP is a transmembrane protein that shares 25% sequence identity with IL-1RI and is required for IL-1 signal transduction (10). IL-1RAcP does not bind directly to IL-1, but it can be cross-linked to radiolabeled ligands in the presence of IL-1RI (9). To address the role of IL-1RAcP, we isolated a human IL-1RAcP cDNA from a placenta cDNA library and used this protein to identify polypeptides having human-specific IL-1RAcP structure and function.

Cited Literature

1. Dinarello, C. A. (1996) Blood 87, 2095–2147; 2. Baeuerle, P. A. & Henkel, T. (1994) Annu. Rev. Immunol. 12, 141–179; 3. Cao, Z., et al. (1996) Science 271, 1128–1131; 4. Cao, Z., et al. (1996) Nature 383, 443–446; 5. Rothe, M., et al. (1995) Science 269, 1424–1427; 6. Takeuchi, M., et al. (1996) J. Biol. Chem. 271, 19935–19942; 7. Nakano, H., et al. (1996) J. Biol. Chem. 271, 14661–14664; 8. Fields, S. & Song, O. (1989) Nature 340, 245–246; 9. Greenfeder, S. A., et al. (1995) J. Biol. Chem. 270, 13757–13765; 10. Wesche, H., et al. (1997) J. Biol. Chem. 272, 7727–7731; 11. Ausubel, F. M., et al. (1994) Curr. Prot. Mol. Biol. 1, 9.1.1–9.1.3; 12. Schutze, S., et al. (1992) Cell 71, 765–776; 13. Schindler, U. & Baichwal, V. R. (1994) Mol. Cell. Biol. 14, 5820–5831; 14. Tartagalia, L. A. & Goeddel, D. V. (1992) Immunol. Today 13, 151–153; 15. Croston, G. E., et al. (1995) J. Biol. Chem. 270, 16514–16517; 16. Sims, J. E., et al. (1988) Science 241, 585–589; 17. Guo, C., et al. (1995) J. Biol. Chem. 270, 27562–27568; 18. GroBhans, J., et al. (1994) Nature 372, 563–566; 19. Galindo, R. L., et al. (1995) Development 121, 2209–2218; 20. Morisato, D. & Anderson, K. V. (1995) Annu. Rev. Genet. 29, 371–399; 21. Curtis, B. M., et al. (1989) Proc. Natl. Acad. Sci. USA 86, 3045–3049; 22. Heguy, A., et al. (1992) J. Biol. Chem. 267, 2605–2609; 23. Kuno, K., et al (1993) J. Biol. Chem. 268, 13510–13518; 24. Leung, K. et al. (1994) J. Biol. Chem. 269, 1579–1582.

SUMMARY OF THE INVENTION

The invention provides methods and compositions relating to isolated IL-1RAcP polypeptides, related nucleic acids, polypeptide domains thereof having IL-1RAcP-specific structure and activity and modulators of IL-1RAcP function, particularly MYD88 binding activity and phosphorylation of IL-1RAcP. IL-1RAcP polypeptides can regulate NFκB activation and thus are important regulators of cell function. The polypeptides may be produced recombinantly from transformed host cells from the subject IL-1RAcP polypeptide encoding nucleic acids or purified from mammalian cells. The invention provides isolated IL-1RAcP hybridization probes and primers capable of specifically hybridizing with the disclosed IL-1RAcP gene, IL-1RAcP -specific binding agents such as specific antibodies, and methods of making and using the subject compositions in diagnosis (e.g. genetic hybridization screens for IL-1RAcP transcripts), therapy (e.g. IL-1RAcP inhibitors to inhibit IL-1 signal transduction) and in the biopharmaceutical industry (e.g. as immunogens, reagents for isolating other transcriptional regulators, reagents for screening chemical libraries for lead pharmacological agents, etc.).

BRIEF DESCRIPTION OF THE SEVERAL VIEWS OF THE DRAWING

FIG. 1. Alignment of hIL-1R Acp protein (SEQ ID NO: 2) with mIL-1R protein (SEQ ID NO: 4).

FIGS. 2A–2E. Alignment of mIL-1R Acp cDNA (SEQ ID NO: 3) with hIL-1R Acp cDNA (SEQ ID NO: 1).

DETAILED DESCRIPTION OF THE INVENTION

The nucleotide sequence of a natural cDNA encoding a human IL-1RAcP polypeptide is shown as SEQ ID NO: 1, and the full conceptual translate is shown as SEQ ID NO:2. The IL-1RAcP polypeptides of the invention include one or more functional domains of SEQ ID NO:2, which domains comprise at least 8, preferably at least 16, more preferably at least 32, most preferably at least 64 contiguous residues of SEQ ID NO:2 and have human IL-1RAcP -specific amino acid sequence and activity. IL-1RAcP domain specific activities include MYD88-binding or binding inhibitory activity, phosphorylation of an intracellular portion of IL-1-RAcP or inhibition of phosphorylation, NFκB expression or inhibition of NFκB expression, and IL-1-RAcP specific immunogenicity and/or antigenicity.

IL-1 RAcP-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an IL-1RAcP polypeptide with a binding target is evaluated. The binding target may be a natural intracellular binding target such as an IL-1RACP binding target, an IL-1RAcP regulating protein or other regulator that directly modulates IL-1RAcP activity or its localization; or non-natural binding target such as a specific immune protein such as an antibody, or an IL-1RAcP specific agent such as those identified in screening assays such as described below. IL-1RAcP-binding specificity may be assayed by binding equilibrium constants (usually at least about $10^7$ $M^{-1}$, preferably at least about $10^8$ $M^{-1}$, more preferably at least about $10^9$ $M^{-1}$), by NFκB reporter gene expression, by the ability of the subject polypeptide to be phosphorylated, to elicit IL-1RAcP specific antibody in a heterologous host (e.g a rodent or rabbit), etc.

For example, deletion mutagenesis is used to define functional IL-1RAcP domains that activate NFκB expression in IL-1RAcP-mediated NFκB activation assays. See, e.g. Table 1.

TABLE 1

Exemplary IL-1RAcP deletion mutants capable of NFκB activation.

| Mutant | Sequence | NFκB |
|---|---|---|
| ΔN1 | SEQ ID NO:2, residues 12–570 | + |
| ΔN2 | SEQ ID NO:2, residues 63–570 | + |
| ΔN3 | SEQ ID NO:2, residues 121–570 | + |
| ΔN4 | SEQ ID NO:2, residues 211–570 | + |
| ΔN5 | SEQ ID NO:2, residues 311–570 | + |
| ΔC1 | SEQ ID NO:2, residues 1–550 | + |
| ΔC2 | SEQ ID NO:2, residues 1–540 | + |
| ΔC3 | SEQ ID NO:2, residues 1–530 | + |
| ΔC4 | SEQ ID NO:2, residues 1–520 | + |

Deletion mutagenesis is used to define functional IL-1RAcP domains that are phosphorylated by Janus Kinases (JAKs) in phosphorylation assays. See, e.g. Table 2.

TABLE 2

Exemplary IL-1RAcP mutants defining a phosphorylated domain of IL-1RacP at tyrosine 503.

| Mutant | Sequence | Phosphorylation |
|---|---|---|
| ΔN1 | SEQ ID NO:2, residues 70–570 | + |
| ΔN2 | SEQ ID NO:2, residues 171–570 | + |
| ΔN3 | SEQ ID NO:2, residues 281–570 | + |
| ΔN4 | SEQ ID NO:2, residues 331–570 | + |
| ΔN5 | SEQ ID NO:2, residues 381–570 | + |
| ΔC1 | SEQ ID NO:2, residues 1–550 | + |
| ΔC2 | SEQ ID NO:2, residues 1–512 | + |
| ΔP1 | SEQ ID NO:2, residues 361–512 | + |
| ΔP2 | SEQ ID NO:2, residues 383–512 | + |
| ΔP3 | SEQ ID NO:2, residues 411–509 | + |
| ΔP4 | SEQ ID NO:2, residues 491–509 | + |
| ΔP5 | SEQ ID NO:2, residues 500–509 | + |

In a particular embodiment, the subject domains provide IL-1RAcP-specific antigens and/or immunogens, especially when coupled to carrier proteins. For example, peptides corresponding to IL-1RAcP- and human IL-1RAcP-specific domains are covalently coupled to keyhole limpet antigen (KLH) and the conjugate is emulsified in Freunds complete adjuvant. Laboratory rabbits are immunized according to conventional protocol and bled. The presence of IL-1RAcP-specific antibodies is assayed by solid phase immunosorbant assays using immobilized IL-1RAcP polypeptides of SEQ ID NO:2, see, e.g. Table 3.

TABLE 3

Immunogenic IL-1RAcP polypeptides eliciting IL-1RAcP-specific rabbit polyclonal antibody: IL-1RAcP polypeptide-KLH conjugates immunized per protocol described above.

| IL-1RAcP Polypeptide Sequence | Immunogenicity |
|---|---|
| SEQ ID NO:2, residues 1–14 | +++ |
| SEQ ID NO:2, residues 11–41 | +++ |
| SEQ ID NO:2, residues 55–75 | +++ |
| SEQ ID NO:2, residues 131–146 | +++ |
| SEQ ID NO:2, residues 131–181 | +++ |
| SEQ ID NO:2, residues 147–158 | +++ |
| SEQ ID NO:2, residues 171–184 | +++ |
| SEQ ID NO:2, residues 171–230 | +++ |
| SEQ ID NO:2, residues 181–206 | +++ |
| SEQ ID NO:2, residues 218–232 | +++ |

TABLE 3-continued

Immunogenic IL-1RAcP polypeptides eliciting IL-1RAcP-specific rabbit polyclonal antibody: IL-1RAcP polypeptide-KLH conjugates immunized per protocol described above.

| IL-1RAcP Polypeptide Sequence | Immunogenicity |
|---|---|
| SEQ ID NO:2, residues 235–281 | +++ |
| SEQ ID NO:2, residues 238–252 | +++ |
| SEQ ID NO:2, residues 261–275 | +++ |
| SEQ ID NO:2, residues 271–285 | +++ |
| SEQ ID NO:2, residues 285–311 | +++ |
| SEQ ID NO:2, residues 291–308 | +++ |
| SEQ ID NO:2, residues 321–361 | +++ |
| SEQ ID NO:2, residues 322–338 | +++ |
| SEQ ID NO:2, residues 365–411 | +++ |
| SEQ ID NO:2, residues 339–375 | +++ |
| SEQ ID NO:2, residues 401–431 | +++ |
| SEQ ID NO:2, residues 411–511 | +++ |
| SEQ ID NO:2, residues 501–517 | +++ |
| SEQ ID NO 2, residues 545–563 | +++ |

The claimed IL-1RAcP polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The IL-1RAcP polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to IL-1RAcP polypeptides, preferably the claimed IL-1RAcP polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel IL-1RAcP-specific binding agents include IL-1RAcP-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate IL-1RAcP function, e.g. IL-1RAcP-dependent transcriptional activation.

Accordingly, the invention provides methods for modulating signal transduction involving NFκB in a cell comprising the step of modulating IL-lRAcP activity. The cell may reside in culture or in situ, i.e. within the natural host. For diagnostic uses, the inhibitors or other IL-1RAcP binding agents are frequently labeled, such as with fluorescent, radioactive, chemiluminescent, or other easily detectable molecules, either conjugated directly to the binding agent or conjugated to a probe specific for the binding agent. Exemplary inhibitors include nucleic acids encoding dominant/negative mutant forms of IL-1RAcP, as described above, etc.

The amino acid sequences of the disclosed IL-1RAcP polypeptides are used to back-translate IL-1RAcP polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural IL-1RAcP-encoding nucleic acid sequences ("GCG" software, Genetics Computer Group, Inc, Madison Wis.). IL-1RAcP-encoding nucleic acids used in IL-1RAcP-expression vectors and incorporated into recombinant host cells, e.g. for expression and screening, transgenic animals, e.g. for functional studies such as the efficacy of candidate drugs for disease associated with IL-1RAcP-modulated cell function, etc.

The invention also provides nucleic acid hybridization probes and replication/amplification primers having a IL-1RAcP cDNA specific sequence comprising at least 12, preferably at least 24, more preferably at least 36 and most preferably at least 96 contiguous bases of a strand of SEQ ID NO:1 sufficient to specifically hybridize with a second nucleic acid comprising the complementary strand of SEQ ID NO:1. Demonstrating specific hybridization generally requires stringent conditions, for example, (Condition I) hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; (Condition II) preferably hybridizing in a buffer comprising 50% formamide in 5×SSPE buffer at a temperature of 42° C. and remaining bound when subject to washing at 42° C. with 0.2×SSPE buffer at 42° C.

TABLE 4

Exemplary IL-1RAcP nucleic acids which hybridize with a strand of SEQ ID NO:1 under Conditions I and/or II.

| IL-1RAcP Nucleic Acids | Hybridization |
|---|---|
| SEQ ID NO:1, nucleotides 1–55 | + |
| SEQ ID NO:1, nucleotides 56–95 | + |
| SEQ ID NO:1, nucleotides 96–128 | + |
| SEQ ID NO:1, nucleotides 133–165 | + |
| SEQ ID NO:1, nucleotides 166–205 | + |
| SEQ ID NO:1, nucleotides 207–248 | + |
| SEQ ID NO:1, nucleotides 250–300 | + |
| SEQ ID NO:1, nucleotides 305–350 | + |
| SEQ ID NO:1, nucleotides 355–400 | + |
| SEQ ID NO:1, nucleotides 405–456 | + |
| SEQ ID NO:1, nucleotides 460–515 | + |
| SEQ ID NO:1, nucleotides 520–591 | + |
| SEQ ID NO:1, nucleotides 595–645 | + |
| SEQ ID NO:1, nucleotides 646–685 | + |
| SEQ ID NO:1, nucleotides 690–775 | + |
| SEQ ID NO:1, nucleotides 785–855 | + |
| SEQ ID NO:1, nucleotides 860–955 | + |
| SEQ ID NO:1, nucleotides 965–1057 | + |
| SEQ ID NO:1, nucleotides 1058–1105 | + |
| SEQ ID NO:1, nucleotides 1108–1175 | + |
| SEQ ID NO:1, nucleotides 1180–1300 | + |
| SEQ ID NO:1, nucleotides 1305–1435 | + |
| SEQ ID NO:1, nucleotides 1436–1530 | + |
| SEQ ID NO:1, nucleotides 1528–1625 | + |
| SEQ ID NO:1, nucleotides 1622–1662 | + |
| SEQ ID NO:1, nucleotides 1625–1705 | + |
| SEQ ID NO:1, nucleotides 1701–1740 | + |

The subject nucleic acids are of synthetic/non-natural sequences and/or are isolated, i.e. unaccompanied by at least some of the material with which they are associated in their natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which they are joined to on a natural chromosome. Recombinant nucleic acids comprising the nucleotide sequence of SEQ ID NO:1, or requisite fragments thereof, contain such sequence or fragment at a terminus, immediately flanked by (i.e. contiguous with) a sequence other than that which they are joined to on a natural chromosome, or flanked by a native flanking region fewer than 10 kb, preferably fewer than 2 kb, which is at a terminus or is immediately flanked by a sequence other than that which they are joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of IL-1RAcP genes and gene transcripts and in detecting or amplifying nucleic acids encoding additional IL-1RAcP homologues and structural analogs. In diagnosis, IL-1RAcP hybridization probes find use in identifying wild-type and mutant IL-1RAcP alleles in clinical and laboratory samples. Mutant alleles are used to generate allele-specific oligonucleotide (ASO) probes for high-throughput clinical diagnoses. In therapy, therapeutic IL-1RAcP nucleic acids are used to modulate cellular expression or intracellular concentration or availability of active IL-1RAcP.

The invention provides efficient methods of identifying agents, compounds or lead compounds for agents active at the level of a IL-1RAcP modulatable cellular function. Generally, these screening methods involve assaying for compounds that modulate IL-1RAcP interaction with a natural IL-1RAcP binding target, such as MYD88. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an IL-1RAcP polypeptide, which may be part of a fusion product with another peptide or polypeptide, e.g. a tag for detection or anchoring, etc. The assay mixtures comprise a natural intracellular IL-1RAcP binding target. While native full-length binding targets may be used, it is frequently preferred to use portions (e.g. peptides) thereof so long as the portion provides binding affinity and avidity to the subject IL-1RAcP polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the IL-1RAcP polypeptide specifically binds the cellular binding target, portion or analog with a reference binding affinity. The mixture components can be added in any order that provides for the requisite bindings and incubations may be performed at any temperature that facilitates optimal binding. Incubation periods are likewise selected for optimal binding but also minimized to facilitate rapid, high-throughput screening.

After incubation, the agent-biased binding between the IL-1RAcP polypeptide and one or more binding targets is detected by any convenient way. A difference in the binding affinity of the IL-1RAcP polypeptide to the target in the absence of the agent as compared with the binding affinity in the presence of the agent indicates that the agent modulates the binding of the IL-1RAcP polypeptide to the IL-1RAcP binding target. Analogously, in the cell-based assay also described below, a difference in IL-1RAcP-dependent transcriptional activation in the presence and absence of an agent indicates the agent modulates IL-1RAcP function. A difference, as used herein, is statistically significant and preferably represents at least a 50%, more preferably at least a 90% difference.

In vitro kinase assays employ an IL-1RAcP peptide substrate to be tested for its ability to be phosphorylated. The assay also requires a tyrosine kinase capable of phosphorylating the substrate at an appropriate tyrosine residue, for example JAK kinase, phosphate-γATP or radiolabeled phosphate-γATP, and appropriate buffers for the kinase reaction. The reaction may also proceed in the presence of an anchor on the surface of the reaction chamber that can bind a molecule attached to the substrate, for example steptavidin on the surface of the chamber, and biotin attached to the substrate. Microwells are coated with streptavidin, and the substrate is conjugated to biotin. The conjugated substrate is placed in the microwell. JAK kinase and phosphate-γATP (labeled or not) are added with appropriate buffers for the reaction. The reaction is allowed to proceed and then stopped and washed. The degree of phosphorylation of the peptide substrate is monitored by assaying the incorporation of radioactive phosphate into the peptide substrate, where the phosphate-γATP is radiolabeled. Where the phosphate-γATP is not labeled, the phosphorylated tyrosine can be detected with labeled anti-phosphotyrosine antibodies. The phosphorylation can also be measured indirectly by observing phosphorylation of a coexpressed substrate, for example by mobility shift on an SDS gel. An appropriate positive control is a reaction with a substrate that is phosphorylated by JAK kinase in the reaction conditions.

The following experimental section and examples are offered by way of illustration and not by way of limitation.

EXAMPLES

Isolation of human IL-1RI cDNA. A cDNA fragment encoding the intracellular portion of the mouse IL-1RAcP was obtained by polymerase chain reaction and used as a hybridization probe to isolate the human IL-1RAcP cDNA from a lambda phage cDNA library made from placenta (Clontech).

Construction of expression plasmids. The expression plasmids for IL-1RAcP and AcP(1–403) were constructed by inserting PCR generated cDNA fragments lacking coding sequence for the signal peptide into the mammalian expression vector pFlag-CMV-1 (Kodak International Biotechnologies, Inc.), which contains the preprotrypsin leader sequence for transient expression of amino-terminal FLAG fusion proteins on the surface of mammalian cells.

Transfection, EMSA and luciferase reporter assay. For EMSA, $2 \times 10^6$ 293 cells were plated in 100 mm dishes and transfected with 5 µg of the indicated plasmid DNA by calcium phosphate precipitation method (11). Nuclear extracts were prepared 24 hours after transfection (12) and tested for activity that would shift the electrophoretic mobility of a [$^{32}$P]-radiolabeled oligonucleotide containing an NF-κB binding site derived from the human ELAM-1 promoter (13). For luciferase reporter assay, $2 \times 10^5$ 293 or HeLa cells were seeded on 35 mm dishes and transfected on the following day with indicated expression plasmids, together with 0.5 µg of ELAM-1 luciferase reporter plasmid (13) and 0.05 µg of a CMV-p-galactosidase plasmid for monitoring transfection efficiency. 24 hours after transfection, cells were treated with 10 ng/ml of IL-1β or TNFα for 6 hours and luciferase activity measured using reagents from Promega.

Coimmunoprecipitation and immunoblotting analysis. $4 \times 10^7$ 293IL-1RI (3) or HeLa cells were used for coimmunoprecipitation of endogenous proteins. For coprecipitation of transfected proteins, $2 \times 10^6$ 293 or 293IL-1RI cells were plated on 100 mm dishes and transfected with 5 µg of expression plasmids. after 20–24 hours, the cells were collected, induced with IL-1β (100 ng/ml) for 3–5 min. and lysed as described previously (3). The immunoprecipitates were prepared using the appropriate antiserum and protein A or protein G conjugated to sepharose beads for 2–4 hours at 4° C. The beads were washed six times with cell lysis buffer (3), and boiled in 20 µl of SDS sample buffer. Solubilized proteins were fractionated on 8% SDS-polyacrylamide gels, and immunoblotted with polyclonal antiserum to IRAK or to IL-IR1. The reactive proteins were detected with ECL reagents (Amersham).

Transient coexpression of IL-1RI and IL-1RAcP activates NF-κB. Unlike the TNF receptor 1 or 2 which signals through ligand-induced homotrimerization (14), overexpression of IL-1RI does not result in ligand-independent NF-κB activation (15), suggesting that aggregation of IL-1RI alone is insufficient for signaling. We tested whether coexpression of IL-1RI and IL-1 RAcP would activate NF-κB. Transient expression of either IL-1RI or IL-1RAcP alone did not result in ligand-independent induction of an NF-κB-dependent luciferase reporter gene in 293 cells. However, coexpression of both proteins resulted in a 20-fold increase in activation of NF-κB activity. The reporter assay results were confirmed by electrophoretic mobility shift assays (EMSA). In cells that coexpressed IL-1RI and IL-1RAcP, NF-κB DNA binding activity was elevated to a level comparable to that induced by IL-1. These data suggest that aggregation of IL-1RI and IL-1RACP as a result of protein overexpression can elicit a signaling pathway leading to NF-κB activation.

IRAK was activated with overexpression of IL-1RI and IL-1RAcP which activates NF-κB by engaging the same signaling pathway that is activated by IL-1. Evidence for IRAK's activation is its own phosphorylation that retards its mobility in an SDS gel (3). In cells coexpressing IL-1RI and IL-1RAcP, two species of IRAK protein were detected by immunoblotting, an 80 kD form that corresponds to unphosphorylated IRAK and an 100 kD form that corresponds to phosphorylated IRAK. The phosphorylated form was not detected in cells that expressed IL-1 RI or IL-1RAcP alone, nor was it detected in the cells coexpressing IL-1RI and a truncated form of IL-1RACP[AcP(1–403)] in which most of the intracellular domain of the protein has been deleted. Compared with the full length IL-1RAcP, similar amounts of AcP(1–403) were expressed on the cell surface as indicated by flow cytometry. Thus, coexpression of IL-1RI and IL-1RACP triggers a pathway similar to that activated by IL-1, and this IRAK activation requires the intracellular domain of IL-1RAcP.

IL-1 induces the association of IL-1RI and IL-1RacP. IL-1 RI and IL-1RAcP form a complex upon IL-I treatment of cells. Rabbit polyclonal antiserum raised to the extracellular domain of IL-1RAcP can immunoprecipitate IL-1RAcP from protein extracts of 293 cells stably transfected with expression plasmid DNA for IL-1RI (293IL-1RI). IL-1RI was detected by immunoblotting in the IL-1RAcP immunocomplex obtained from IL-1 treated, but not untreated 293IL-1RI cells, indicating that the association of the endogenous IL-1RAcP with IL-1RI is ligand-dependent. The intracellular portion of the IL-1RAcP is necessary for its association with IL-1RI. 293IL-1RI cells were transiently transfected with expression vectors for epitope-tagged IL-1RAcP or AcP(1–403), and treated briefly with IL-1 or left untreated. Immunoprecipitation of the transiently expressed IL-1RAcP coprecipitated IL-1RI in the absence of IL-1 induction. However, the amount of coprecipitating IL-1RI was enhanced significantly by IL-1. The formation of IL-1 RI and IL-1 RAcP complex prior to IL-1 treatment is due to overexpression of the two transmembrane proteins. This observation is consistent with the activation of IRAK and NF-κB observed in cells that transiently coexpress the two receptor chains. The association of IL-1RI and AcP (1–403) was not evident in untreated cells, but was readily detectable in IL-1 treated cells. Thus both extra- and intracellular domains of IL-1RAcP play a role in the formation of the active receptor complex. Since IL-1 binds directly to IL-1RI (16) and can be cross-linked to IL-1RAcP (4), the initial step of IL-1 signaling is a ligand-mediated association of IL-IR1 and IL-1RAcP through their extracellular domains. The complex is then further stabilized through their cytoplasmic domains, which is accomplished by other associated molecules.

Immunoprecipitation of IL-1RAcP coprecipiates IRAK. It is known that IRAK coimmunoprecipitates with IL-1RI after IL-1 induction (3). If IL-1RAcP forms complexes with IL-1RI after IL-1 treatment, then immunoprecipitation of IL-1RAcP should also coprecipitate IRAK. IRAK was indeed readily detected in immunoprecipitates of both IL-1RAcP and IL-1RI from IL-1-treated, but not untreated, 293IL-1RI and HeLa cells. To show that IL-1RAcP is responsible for recruiting IRAK to the receptor complex, IL-1RAcP or IL-1RI was transiently expressed in 293 cells, and tested for their ability to coprecipitate endogenous IRAK. By immunoblotting, IRAK was found to coprecipitate only with IL-1 RAcP but not with IL-1 RI. AcP(1–403) lacking most of the intracellular domain failed to coprecipitate IRAK, a result consistent with the inability of this mutant to activate IRAK. IL-1 signaling requires the oligomerization of IL-1RI as determined by fluorescence resonance energy transfer analysis (17), and the signaling receptor complex contains aggregated IL-1RAcP that indirectly recruits IRAK to the complex.

AcP(1–403) blocks recruitment of IRAK to the receptor and IL-1 signaling. Since AcP(1–403) can be recruited to IL-1RI by the ligand, yet is unable to bind to IRAK, when overexpressed, this polypeptide impedes the association of endogenous IL-1RAcP with IL-1RI and, thereby, prevents the recruitment of IRAK to the receptor complex. Indeed, the amount of IRAK protein detected in IL-1RI immunoprecipitates was markedly reduced in HeLa cells transiently transfected with expression plasmid for AcP(1–403). Consistently, transfixing HeLa cells with the expression plasmid for AcP (1–403) resulted in a dose-dependent inhibition of IL-1 induced NF-κB activation as determined by luciferase reporter assay. Under the same conditions, AcP (1–403) overexpression had no effect on TNF mediated NF-κB activation, indicating that the observed inhibition is specific to IL-1 signal transduction.

Thus, IL-1 signals by aggregating the cell surface molecules, IL-1RI and IL-1RAcP. While the former conveys high affinity ligand binding (16), the latter plays a role in recruiting IRAK to the receptor complex, an event that correlates strictly with IL-1 induced NF-κB activation (15). Although when overexpressed and aggregated by antibody, IL-1RAcP coprecipitated IRAK in unstimulated cells, IRAK is not associated with IL-1RAcP prior to IL-1 treatment. In both HeLa and 293IL-1RI cells where IL-1RAcP is not overexpressed, the association of IRAK with IL-1RAcP is dependent on IL-1 treatment. IL-1RI alone is insufficient for binding IRAK and for signaling, although its intracellular domain is required for IL-1 mediated NF-κB activation (15, 21–24). When complexed with IL-1RAcP, IL-1RI provides docking sites for other signaling molecules to permit IRAK binding to the complex. The observation that aggregated IL-1RAcP, but not IL-1RI, can bind to IRAK indicates that IL-1 RAcP is a primary component responsible for recruiting the kinase.

Protocol for Cell-Based IL-1RAcP-MYD88 Interaction assay. IL-1RAcP is identified as a MYD88-interacting protein by coprecipitation assay: 293 cells are transfected with mammalian expression vectors encoding Flag-tagged MYD88 and Myc-tagged IL-1RAcP respectively. After 48 hours, cells are collected, washed twice with phosphate-buffered saline and lysed for 30 min at 4° C. in 0.5 ml of lysis buffer (50 mM HEPES pH 7.6, 100 mM NaCl, 1% NP-40, 1 mM EDTA, 10% glycerol) containing phosphatase and protease inhibitors. Cellular debris are removed by centrifugation at 10,000×g for 10 min twice. The NaCl concentration of the cell lysates is increased to 250 mM. The cell lysates are incubated for 1 hour on ice with 1 μg of anti-Flag monoclonal antibody or control mouse IgG1 antibody, and an additional hour at 4° C. with 15 ml of protein G-agarose beads. The beads are then collected, and washed four times with 1 ml of lysis buffer containing 250 mM NaCl. The bound proteins are eluted, fractionated by SDS-PAGE and analyzed by western blotting using anti-Myc or anti-Flag polyclonal antibodies. The immunoblot is developed with horseradish peroxidase-coupled goat anti-rabbit immunoglobin as secondary antibody and visualized using the Enhanced Chemoluminescence (ECL) Detection System.

Protocol for Cell-Based NF-κB Reporter Assay. IL-1RAcP can trans-activate NF-κB reporter constructs when overexpressed in 293 cells or HeLa cells. 293 cells are transfected using the calcium phosphate precipitation method with a plasmid encoding a 6 NF-κB-luciferase reporter construct and various amounts of expression vector encoding IL-1RAcP. After 36–48 hours, cells are left untreated or treated with IL-1 (10–50 ng/ml) or TNF (50–100 ng) for 6 hours prior to harvest. Cells are lysed and luciferase activity measured using the luciferase assay kit (Promega). The luciferase activity in each transfection is normalized by co-transfecting a pRSV-β gal control vector. Protocol for high throughput in vitro IL-lRAcP -MYD88 binding assay.

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P IL-1RAcP polypeptide 10× stock: $10^{-8}$–$10^{-6}$M "cold" IL-1RAcP (truncated intracellular C-terminal domain) supplemented with 200,000–250,000 cpm of labeled IL-1RAcP (Beckman counter). Place in the 4° C. microfridge during screening.

Protease inhibitor cocktail (1OOOX): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2mM NaVO$_3$ (Sigma # S-6508) in 10 ml of PBS.

MYD88: $10^{-7}$–$10^{-5}$ M biotinylated MYD88 in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-IL-1RAcP (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 μM biotinylated MYD88(0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls for all assays (located on each plate):

a. Non-specific binding b. Soluble (non-biotinylated MYD88) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising the amino acid sequence set forth as SEQ ID NO:2, or a fragment thereof comprising at least one of the amino acid sequences set forth as residues 321–361, residues 339–375, and residues 491–509 of SEQ ID NO: 2.

2. The polypeptide of claim 1, comprising the amino acid sequence set forth as residues 411–511 of SEQ ID NO:2.

3. The polypeptide of claim 1, comprising at least one of the amino acid sequences set forth as residues 1–520 and residues 381–570 of SEQ ID NO:2.

4. The polypeptide of claim 1, comprising the amino acid sequence set forth as SEQ ID NO:2.

5. A method of screening for an agent that modulates the interaction of an IL-1RAcP polypeptide to a binding target, said method comprising the steps of:
incubating a mixture comprising:
a polypeptide according to claim 1,
a binding target of said polypeptide, and
a candidate agent;
under conditions whereby, but for the presence of said agent, said polypeptide specifically binds said binding target at a reference affinity;
detecting the binding affinity of said polypeptide to said binding target to determine an agent-biased affinity, wherein a difference between the agent-biased affinity and the reference affinity indicates that said agent modulates the binding of said polypeptide to said binding target.

6. An isolated or recombinant nucleic acid encoding a polypeptide comprising the amino acid sequence set forth as SEQ ID NO:2, or a fragment thereof comprising at least one the amino acid sequences set forth as residues 321–361, residues 339–375, and residues 491–509 of SEQ ID NO: 2.

7. The nucleic acid of claim 6 encoding a polypeptide comprising the amino acid sequence set forth as residues 411–511 of SEQ ID NO:2.

8. The nucleic acid of claim 6 encoding a polypeptide comprising at least one of the amino acid sequences set forth as residues 1–520 and residues 381–570 of SEQ ID NO:2.

9. The nucleic acid of claim 6 encoding a polypeptide comprising the amino acid sequence set forth as SEQ ID NO:2.

10. A cell comprising a recombinant nucleic acid according to claim 6.

11. An isolated or recombinant nucleic acid comprising the polynucleotide sequence set forth as SEQ ID NO:1, or a fragment thereof comprising at least one of the polynucleotide sequences set for as nucleotides 965–1057 and nucleotides 1436–1530 of SEQ ID NO:1.

12. The nucleic acid of claim 11 comprising the polynucleotide sequence set forth as nucleotides 965–1057 of SEQ ID NO:1.

13. The nucleic acid of claim 11 comprising the polynucleotide sequence set forth as nucleotides 1436–1530 of SEQ ID NO:1.

14. The nucleic acid of claim 11 comprising the polynucleotide sequence set forth as SEQ ID NO:1.

15. A cell comprising a recombinant nucleic acid according to claim 11.

* * * * *